United States Patent [19]

Granirer et al.

[11] Patent Number: 4,759,930
[45] Date of Patent: Jul. 26, 1988

[54] INSECT KILLING COMPOSITIONS AND METHOD OF KILLING INSECTS EMPLOYING A SYNERGISTIC MIXTURE OF PYRETHRUM, EUCALPYTUS, ROSEMARY AND PEPPERMINT

[76] Inventors: Marc S. Granirer; Dustin S. Nelson, both of 1547 N. Curson Ave., Los Angeles, Calif. 90046

[21] Appl. No.: 60,105

[22] Filed: Jun. 9, 1987

[51] Int. Cl.⁴ ..................... A01N 59/14; A01N 65/00
[52] U.S. Cl. ...................................... 424/148; 514/65; 424/195.1
[58] Field of Search ................. 424/148, 195.1; 514/65

[56] References Cited

U.S. PATENT DOCUMENTS

| | | | |
|---|---|---|---|
| 496,110 | 4/1893 | Brown | 424/148 |
| 929,963 | 8/1909 | Lyda et al. | 424/148 |
| 1,029,203 | 6/1912 | Loewenthal | 424/148 |
| 1,636,688 | 7/1927 | Harris | 424/148 |
| 4,438,090 | 3/1984 | Brite | 424/148 |
| 4,518,593 | 5/1985 | Juvin et al. | 424/195.1 |
| 4,587,123 | 5/1986 | Price | 424/195.1 |

FOREIGN PATENT DOCUMENTS 455978 10/1936 United Kingdom .

OTHER PUBLICATIONS

"The World Book Encyclopedia," vol. 4, published by Field Enterprises Educational Corp., (1965), p. 601.
"The World Book Encyclopedia," vol. 10, published by Field Enterprises Educational Corp., (1965), pp. 224-225.
C.A., vol. 82, (1975), 107564g.
Hagiwara, C.A., vol. 93, (1986), 93:127,150z.
Ahmed et al., C.A., vol. 105, (1986), 105:129,423f.

Primary Examiner—Allen J. Robinson
Attorney, Agent, or Firm—Kendrick, Lorig & Bright

[57] ABSTRACT

Insect-killing compositions comprise pyrethrum, rotenone, or both, and one or more of the following: eucalyptus, rosemary, peppermint and boric acid. These compositions, in powder form, used in small amounts, kill insects such as adult and immature cockroaches in large numbers, yet are, where no boric acid is present, relatively innocuous to most human beings and animals.

5 Claims, No Drawings

INSECT KILLING COMPOSITIONS AND METHOD OF KILLING INSECTS EMPLOYING A SYNERGISTIC MIXTURE OF PYRETHRUM, EUCALPYTUS, ROSEMARY AND PEPPERMINT

This invention relates to compositions effective for killing insects, especially cockroaches, and methods for utilizing these compositions to kill such insects.

The insect-killing compositions of this invention comprise pyrethrum or rotenone, or both, and one or more substances selected from the group consisting of eucalyptus, rosemary, peppermint and boric acid.

In preferred embodiments, these compositions are powders made by pulverizing and blending the components of the compositions, as by using a blender or grinder. Such powders preferably comprise particles of substantially uniform size, and sufficiently small for insects such as immature and adult cockroaches to ingest.

In preferred embodiments, these compositions include pyrethrum or rotenone, or both, in substantial amounts, preferably in a major amount by weight. Pyrethrum is a substance from the Composite family, called Compositae, and is of the genus Chrysanthemum. Two preferred species are the Persian species, called C. Coccineum and the Dalmation species, called C. Cinerariaefolium. Preferably, the pyrethrum is utilized in these compositions in the form of seeds, flowers or leaves, most preferably in the form of flowers alone, leaves alone, or flowers and leaves combined. Rotenone comes from certain tropical plant roots.

Eucalyptus is a substance from the Myrtle family, called Myrtaceae, and is of the genus Eucalyptus. Two preferred species of eucalyptus for these compositions are the Blue Gum species called *E. globulus* and the Jarrah species called *E. marginata*.

Rosemary is a substance from the Mint family called Labiatae. The preferred genus is Rosemarinus, and the preferred species, *R. officinalis*.

Peppermint is a substance from the mint family, called Labiatae. The preferred genus for use in these compositions is Mentha; the preferred species, *M. piperita*.

Boric acid is a substance widely available commercially. The preferred form of boric acid in these compositions is a powder of substantially 100% purity.

In preferred embodiments, these compositions include from 10% to 100% by volume of pyrethrum or rotenone, or both, from 5% to 50% by volume of eucalyptus, from 5% to 50% by volume of rosemary, from 5% to 50% by volume of peppermint, and from 0% to 90% by volume of boric acid. Where the compositions comprise pyrethrum or rotenone, or both, in combination with fewer than all of the other four constituents, the pyrethrum or rotenone, or both, preferably comprise from 10% to 100% by volume of the composition, and the one, two or three other constituents preferably comprise, from 1% to 90% by volume of the composition.

These compositions are deadly to insects and especially to cockroaches of all species, whether the cockroaches are adult or immature. However, these compositions are relatively innocuous to most humans and animals, and where no boric acid is present, can be ingested by human adults, children and animals, with substantially no adverse effects.

These compositions are used to kill insects such as cockroaches by placing the powder, in loose form or in a container, in areas where cockroaches are regularly found or seen. The powder is used in widely varying amounts but preferably in an amount sufficient to kill insects such as cockroaches in substantial numbers in a period of two to seven days.

The following examples show that these compositions, made by pulverizing and blending the components of the composition in a blender or grinder, were effective in killing cockroaches.

Each of the examples shows the composition used, and the results obtained. In each case, we formed the composition in the same way, i.e., by pulverizing and blending the constituents into a power. All percentages are by volume.

In each of the examples, approximately one tablespoon of cockroach-killing powder was sprinkled atop paper towels placed in the bottom of a pan. The cockroaches were then placed in the pan, and the pan was covered with plastic wrap having sufficient air holes in it to permit the cockroaches to breathe and survive. The cockroaches used were Asian, the most common and the hardiest. We kept each test pan at room temperature and checked it daily.

EXAMPLE 1

Cockroach-killing composition: Boric Acid 50%, Eucalyptus - 50%

Cockroach specimens placed in pan: 3 baby cockroaches

Day 1: 3 are fine.
Day 2: 1 is fine; 1 is very slow; 1 is almost dead.
Day 3: 1 is fine; 1 is very slow; 1 is dead.
Day 4: 2 are almost dead; 1 is dead.
Day 5: 3 are dead.

EXAMPLE 2

Cockroach-killing composition: Eucalyptus—20%, Rosemary—20%, Peppermint—20%, Boric Acid—20%, Borax—20%

Cockroach specimens placed in pan: 1 adult cockroach and 1 baby cockroach

Day 1: Both are fine.
Day 2: Baby is fine; adult is extremely slow.
Day 3: Baby is fine; adult is dead.

EXAMPLE 3

Cockroach—killing composition: Eucalyptus—33.3%, Boric Acid—33.3%, Borax—33.3%

Cockroach specimens placed in pan: 3 baby cockroaches

Day 1: 3 are fine.
Day 2: 1 is dead, 2 are fine.
Day 3: 1 is dead, 2 are fine.
Day 4: 1 is dead, 1 is fine, 1 is very slow.

EXAMPLE 4

Cockroach—killing composition: Eucalyptus—25%, Rosemary—25%, Peppermint—25%, Boric Acid—25%

Cockroach specimens spaced in pan: 3 baby cockroaches

Day 1: 3 are fine.
Day 2: 2 are dead, 1 is fine.
Day 3: 3 are dead.

EXAMPLE 5

Cockroach—killing composition: Boric Acid—100% (same as some products on the market)
Cockroach specimens placed in pan: 1 adult cockroach, 2 baby cockroaches
Day 1: 3 are fine.
Day 2: Adult is fine; 1 baby is dead; 1 baby is almost dead.
Day 3: Adult is fine; 1 baby is dead; 1 baby is almost dead.
Day 4: Adult is fine; 1 baby is dead; 1 baby is almost dead.
Day 5: Adult is fine; 1 baby is dead; 1 baby is almost dead.
Day 6: Adult is almost dead; 1 baby is almost dead; 1 baby is dead.
Day 7: Adult is almost dead; 1 baby is almost dead; 1 baby is dead.
Day 8: All are dead.

EXAMPLE 6

Cockroach—killing composition: Boric Acid—33.3%, Borax—33.3%, Baking Soda—33.3% Cockroach specimens placed in pan: 1 adult cockroach, 2 baby cockroaches
Day 1: 3 are fine.
Day 2: Adult is fine; 2 babies are dead.
Day 3: Adult is fine; 2 babies are dead.
Day 4: Adult is fine; 2 babies are dead.
Day 5: Adult is fine; 2 babies are dead.
Day 6: Adult is fine; 2 babies are dead.
Day 7: Adult is fine; 2 babies are dead.
Day 8: Adult is slow; 2 babies are dead.
Day 9: Adult is slow; 2 babies are dead.
Day 10: All are dead.

EXAMPLE 7

Cockroach-killing composition: Baking soda 100%
Cockroach specimens placed in pan: 1 adult cockroach, 2 baby cockroaches
Day 1: 3 are fine.
Day 2: Adult is fine; 2 babies are dead.
Day 3: Adult is fine; 2 babies are dead.
Day 4: Adult is fine; 2 babies are dead.
Day 5: Adult is fine; 2 babies are dead.
Day 6: Adult is fine; 2 babies are dead.
Day 7: Adult is fine; 2 babies are dead.
Day 8: Adult is fine; 2 babies are dead.
Day 9: Adult is fine; 2 babies are dead.
Day 10: Adult is very slow; 2 babies are dead.
Day 11: All are dead.

EXAMPLE 8

Cockroach—killing composition: Borax—100%
Cockroach specimens placed in pan: 1 adult cockroach, 1 baby cockroach
Day 1: 2 are alive.
Day 2: 2 are alive.
Day 3: 2 are alive.
Day 4: 2 are alive.
Day 5: 2 are alive.
Day 6: Both are almost dead.
Day 7: Adult is almost dead; baby is dead.
Day 8: Both are dead.

EXAMPLE 9

Cockroach—killing composition: Boric Acid—50%, Borax - 50%
Cockroach specimens placed in pan: 1 adult cockroach, 2 baby cockroaches
Day 1: 3 are alive.
Day 2: Adult is fine; 2 babies are dead.
Day 3: Adult is slow; 2 babies are dead.
Day 4: Adult is very slow and almost dead; 2 babies are dead.
Day 5: All are dead.

EXAMPLE 10

Cockroach—killing composition: Eucalyptus—33.3%, Rosemary—33.3%, Peppermint—33.3%
Cockroach specimens placed in pan: 1 adult cockroach
Day 1: Adult is fine.
Day 2: Adult is fine.
Day 3: Adult is fine.
Day 4: Adult is fine.
Day 5: Adult is fine.
Day 6: Adult is fine.
Day 7: Adult is fine.
Day 8: Adult is slow.
Day 9: Adult is slow.
Day 10: Adult is slow.

EXAMPLE 11

Cockroach—killing composition: Eucalyptus—100%
Cockroach specimens placed in pan: 1 adult cockroach; 3 baby cockroaches
Day 1: Adult is fine.
Day 2: Adult is fine.
Day 3: Adult is fine.
Day 4: Adult is fine.
Day 5: Adult is fine.
Day 6: Adult is fine.
Day 7: Adult is fine.
Day 8: Adult is fine.
Day 9: Adult is fine.
Day 10: Adult is fine.

EXAMPLE 12

Cockroach—killing composition: Peppermint—100%
Cockroach specimens placed in pan: 3 baby cockroaches
Day 1: All are fine.
Day 2: All are fine.
Day 3: All are fine.
Day 4: All are fine.
Day 5: All are fine.
Day 6: All are fine.
Day 7: All are fine.
Day 8: All are fine.
Day 9: All are fine.
Day 10: All are fine.

EXAMPLE 13

Cockroach—killing composition: Rosemary—100%
Cockroach specimens placed in pan: 3 baby cockroaches
Day 1: All are fine.
Day 2: All are fine.
Day 3: All are fine.
Day 4: All are fine.

Day 5: All are fine.
Day 6: All are fine.
Day 7: All are fine.
Day 8: All are fine.
Day 9: All are fine.
Day 10: All are fine.

EXAMPLE 14

Cockroach—killing composition: Boric Acid—100%
Cockroach specimens placed in pan: 2 adult cockroaches
Day 1: Both are fine.
Day 2: Both are slow.
Day 3: Both are very slow.
Day 4: 1 is almost dead; 1 is slow.
Day 5: 1 is dead; 1 is slow.
Day 6: 1 is dead; 1 is almost dead.
Day 7: 1 is dead; 1 is almost dead.
Day 8: Both are dead.

EXAMPLE 15

Cockroach—killing composition: Boric Acid—10%, Eucalyptus—30%, Rosemary—30%, Peppermint—30%
Cockroach specimens placed in pan: 2 adult cockroaches
Day 1: Both are slow.
Day 2: Both are slow.
Day 3: 1 is almost dead; 1 is slow.
Day 4: Both are almost dead.
Day 5: Both are dead.

EXAMPLE 16

Cockroach—killing composition: Boric Acid—25%, Eucalyptus—25%, Rosemary—25%, Peppermint—25%
Cockroach specimens placed in pan: 2 adult cockroaches
Day 1: Both are a little slow.
Day 2: 1 is almost dead; 1 is slow.
Day 3: 1 is dead; 1 is very slow.
Day 4: 1 is dead; 1 is very slow
Day 5: 1 is dead; 1 is very slow.
Day 6: 1 is dead; 1 is very slow
Day 7: Both are dead.

EXAMPLE 17

Cockroach—killing composition: Boric Acid—50%, Eucalyptus—16.66%, Rosemary—16.66%, Peppermint—16.66%
Cockroach specimens placed in pan: 2 adult cockroaches
Day 1: Both are fine.
Day 2: Both are a little slow.
Day 3: 1 is slow; 1 is very slow.
Day 4: Both are very slow.
Day 5: Both are very slow.
Day 6: 1 is almost dead; 1 is very slow.
Day 7: 1 is dead; 1 is almost dead.
Day 8: Both are dead.

EXAMPLE 18

Cockroach—killing composition: Boric Acid—75%; Eucalyptus—8.33%, Rosemary—8.33%; Peppermint—8.33%
Cockroach specimens placed in pan: 2 adult cockroaches
Day 1: Both are fine.
Day 2: 1 is slow; 1 is fine.
Day 3: 1 is very slow; 1 is fine.
Day 4: 1 is dead; 1 is fine.
Day 5: 1 is dead; 1 is slow.
Day 6: 1 is dead; 1 is almost dead.
Day 7: Both are dead.

EXAMPLE 19

Cockroach—killing composition: Boric Acid—90%, Eucalyptus—3.33%, Rosemary—3.33%, Peppermint—3.33%
Cockroach specimens placed in pan: 2 adult cockroaches
Day 1: Both are fine.
Day 2: 1 is slow; 1 is fine.
Day 3: 1 is almost dead; 1 is very slow.
Day 4: Both are almost dead.
Day 5: 1 is dead; 1 is barely alive.
Day 6: Both are dead.

EXAMPLE 20

Cockroach—killing composition: Boric Acid—50%, Pyrethum seeds—50%
Cockroach specimens placed in pan: 2 adult roaches
Day 1: Both are fine.
Day 2: Both are fine.
Day 3: Both are fine.
Day 4: 1 is dead; 1 is very slow.
Day 5: 1 is dead; 1 is very slow.
Day 6: Both are dead.

EXAMPLE 21

Cockroach—killing composition: Boric Acid—5%, Rosemary—31.66%, Peppermint—31.66%
Cockroach specimens placed in pan: 3 adult cockroaches
Day 1: All are fine.
Day 2: All are fine.
Day 3: 1 is slow; 2 are fine.
Day 4: 1 is very slow; 2 are slow.
Day 5: 1 is very slow; 2 are slow.
Day 6: 1 is dead; 1 is very slow; 1 is slow.

EXAMPLE 22

Cockroach—killing composition: Pyrethrum Flowers—100%
Cockroach specimens placed in pan: 2 adult cockroaches
Day 1: Both are fine.
Day 2: Both are fine.
Day 3: Both are fine.
Day 4: 1 is dead; 1 is fine.
Day 5: 1 is dead; 1 is fine.
Day 6: 1 is dead; 1 is fine.
Day 7: 1 is dead; 1 is fine.
Day 8: 1 is dead; 1 is fine.

EXAMPLE 23

Cockroach—killing composition: Pyrethrum Leaves—100%
Cockroach specimens placed in pan: 2 adult cockroaches
Day 1: Both are fine.
Day 2: 1 is fine; 1 is slow.
Day 3: 1 is almost dead; 1 is fine.
Day 4: 1 is dead; 1 is fine.
Day 5: 1 is dead; 1 is fine.
Day 6: 1 is dead; 1 is fine.
Day 7: All are dead.

EXAMPLE 24

Cockroach—killing composition: Boric Acid—10%, Pyrethrum Flowers—45%; Eucalyptus—15%, Rosemary—15%, Peppermint—15%

Cockroach specimens placed in pan: 4 adult cockroaches
Day 1: All are fine.
Day 2: All are fine.
Day 3: All are a little slow.
Day 4: 1 is very slow; 3 are slow.
Day 5: 3 are dead; 1 is slow.
Day 6: 3 are dead; 1 is almost dead.
Day 7: All are dead.

EXAMPLE 25

Cockroach—killing composition: Pyrethrum Flowers—50%, Eucalyptus—16.66%, Rosemary—16.66%, Peppermint—16.66% Cockroach specimens placed in pan: 2 adult cockroaches
Day 1: Both are fine.
Day 2: 1 is slow; 1 is fine.
Day 3: 1 is dead; 1 is very slow.
Day 4: Both are dead.

EXAMPLE 26

Cockroach—killing composition: Boric Acid—10%, Pyrethrum Flowers—90% Cockroach specimens placed in pan: 2 adult cockroaches
Day 1: Both are fine.
Day 2: Both are slow.
Day 3: 1 is dead; 1 is barely alive.
Day 4: Both are dead.

What is claimed is:

1. An insect-killing composition comprising, by volume from about 10% to about 90% of pyrethrum and from about 90% to about 10% of eucalpytus, rosemary and peppermint in an effective insecticidal amount of each.

2. The composition of claim 1 further comprising an insecticidally effective amount of boric acid.

3. A method for killing insects comprising placing in areas where insects are present an amount sufficient to kill such insects a composition according to claim 1.

4. The method of claim 3 wherein said composition also includes an insecticidally effective amount of boric acid.

5. The method of claim 3 wherein the insects are cockroaches.

* * * * *